US009763854B2

(12) United States Patent
Oberlin et al.

(10) Patent No.: US 9,763,854 B2
(45) Date of Patent: Sep. 19, 2017

(54) FLOW RESTRICTOR

(71) Applicant: L. Perrigo Company, Allegan, MI (US)

(72) Inventors: Paul D. Oberlin, Kalamazoo, MI (US); Michael S. Reiter, Mattawan, MI (US)

(73) Assignee: L. Perrigo Company, Allegan, MI (US)

( * ) Notice: Subject to any disclaimer, the term of this patent is extended or adjusted under 35 U.S.C. 154(b) by 306 days.

(21) Appl. No.: 14/717,668

(22) Filed: May 20, 2015

(65) Prior Publication Data

US 2016/0338912 A1 Nov. 24, 2016

(51) Int. Cl.

| | |
|---|---|
| ***A61B 19/00*** | (2006.01) |
| ***A61J 1/14*** | (2006.01) |
| ***A61J 1/22*** | (2006.01) |
| ***A61J 1/20*** | (2006.01) |
| ***B65D 47/20*** | (2006.01) |

(52) U.S. Cl.

CPC ........... *A61J 1/1412* (2013.01); *A61J 1/1468* (2015.05); *A61J 1/2096* (2013.01); *A61J 1/22* (2013.01); *B65D 47/2031* (2013.01)

(58) Field of Classification Search

CPC ...... A61J 1/1412; A61J 1/1468; A61J 1/2096; A61J 1/22; B65D 47/2031

See application file for complete search history.

(56) References Cited

U.S. PATENT DOCUMENTS

| | | | |
|---|---|---|---|
| 2,783,908 | A | 3/1957 | Winfield |
| 4,515,752 | A | 5/1985 | Miramanda |
| 4,991,745 | A | 2/1991 | Brown |
| 5,271,531 | A | 12/1993 | Rohr et al. |
| 5,409,144 | A | 4/1995 | Brown |
| 5,839,614 | A | 11/1998 | Brown |
| 7,681,750 | B2 | 3/2010 | Jackel |
| 8,459,312 | B2 | 6/2013 | Manera et al. |
| 8,485,231 | B2 | 7/2013 | Young |
| 8,535,621 | B2 | 9/2013 | Iheme et al. |
| 8,794,489 | B2 | 8/2014 | Bloom et al. |
| 2007/0062906 | A1 | 3/2007 | Morano et al. |
| 2008/0237278 | A1 | 10/2008 | Gaus et al. |
| 2009/0084752 | A1 | 4/2009 | Coulson |
| 2012/0103470 | A1 | 5/2012 | Terwilliger et al. |
| 2012/0104054 | A1 | 5/2012 | Terwilliger et al. |
| 2014/0183154 | A1 | 7/2014 | Essebaggers et al. |
| 2014/0209644 | A1 | 7/2014 | Socier et al. |

*Primary Examiner* — Leslie Deak

(74) *Attorney, Agent, or Firm* — Breiner & Breiner, L.L.C.

(57) ABSTRACT

Flow restrictors for use with a syringe or without a syringe are disclosed for dispensing a liquid medicine for an infant or child. The flow restrictors include a cover having a raised ring, a sleeve for insertion into a bottle, a self-sealing orifice for dispensing the medicine and including an annular cylinder having vertical supports or ribs which extend outward and engage the inside wall of the sleeve. The sleeve includes one or more external protrusions.

12 Claims, 9 Drawing Sheets

FLOW RESTRICTOR

FIELD OF THE INVENTION

The present invention relates to flow restrictors. More particularly, the invention relates to flow restrictors for use in infant and children's liquid medicine bottles.

BACKGROUND OF THE INVENTION

The flow restrictor inventions are directed to use in infant and children's liquid medicine bottles, including for ibuprofen and acetaminophen. Drug accidents may occur if a child resistant cap is not placed back on the medicine bottle and a child consumes more medicine than a prescribed or recommended dose. To prevent such accidents, flow restrictors have been added to the top of the bottle. Such flow restrictors may be used with a syringe inserted into the flow restrictor for removal of the liquid medicine from the bottle and to dispense the medicine to the infant or child; or a flow restrictor wherein when the medicine bottle is squeezed and the flow restrictor has an aperture which opens to dispense the liquid medicine to a dose cup.

For example, two types of flow restrictors now in use consist of (1) a flow restrictor which covers the opening of a bottle, and (2) a flow restrictor used to create a smaller diameter opening in the bottle. However, the flow restrictor used to cover the opening of the bottle may still permit the medicine to leak because, for example, when a cap is screwed onto the bottle, a cap liner may depress the opening causing leakage. Additionally, such a flow restrictor may not effectively grip the neck of the medicine bottle, thereby permitting the flow restrictor to be accidently pulled out of the bottle by an inserted syringe. Additionally, some flow restrictors, positioned flush against the diameter of the mouth of the bottle, have been known to be accidently pushed into the bottle. Further, flow restrictors used to reduce the diameter of the bottle may leak when the bottle is tipped over. Additionally, the squeeze flow restrictors may come off when the bottle is squeezed.

Accordingly, these known flow restrictors have various shortcomings. These and other shortcomings of these devices are addressed by the present invention.

SUMMARY OF THE INVENTION

A primary object of the present invention is to provide improved flow restrictors for use with a liquid medicine bottle which uses a syringe and for use with a liquid medicine bottle which is squeezed to dispense the medicine to a dose cup.

The flow restrictor invention for use with a syringe and without a syringe includes a cover having a flange which seats on the opening of the bottle; the cover includes a raised ring to engage the liner of a cap when the cap is turned onto the bottle; the cover includes an integral downwardly extending sleeve which fits into the neck of the bottle and is configured for a tight seal; and an orifice for dispensing of the medicine. The orifice may be for use with a syringe to dispense the medicine or the orifice may open to dispense the medicine by squeezing the bottle. The raised ring of the cover allows for the cap to be secured tightly to the bottle to assure a good seal without compromising the flow restrictor opening. The orifice on both of the flow restrictors includes a closure which defaults to a closed position. When using the flow restrictor with a syringe, the orifice opens down into the bottle. When a syringe is not used, the bottle is squeezed and the orifice opens out of the bottle. Both flow restrictors include an orifice having a downwardly extending annular cylinder which has vertical supports or ribs which extend outward and engage the inside wall of the sleeve and the sleeve includes one or more external horizontal protrusions. When the cap is screwed onto the bottle, the downward force is transferred by these vertical supports to the external horizontal protrusions, thereby assuring a tight seal to the inside wall of the neck of the bottle neck.

With respect to the flow restrictor not used with a syringe, a thermoplastic elastomer may be used with a polypropylene rigid insert. The flow restrictor has a thicker thermoplastic elastomer around a co-molded connection providing for a more robust component, but has a thinner material for orifice slitting to allow for a manageable pressure to dose the medicine.

The present invention is, therefore, directed to a flow restrictor for a medicine bottle for use with a syringe and without a syringe comprising a cover having a flange adapted to seat on the opening of the bottle. The cover has a raised ring adapted to engage the liner of a cap for the bottle when the cap is turned onto the bottle. The cover further comprises an integral downwardly extending sleeve which fits into a neck of the bottle and is adapted to provide a tight seal. There is a self-sealing orifice for dispensing of the medicine comprising a downwardly extending annular cylinder having vertical supports or ribs which extend outward and engage the inside wall of the sleeve. The orifice has a self-sealing opening for dispensing the medicine. The sleeve further includes one or more external horizontal protrusions. When the cap is screwed onto the bottle, the downward force is transferred by the vertical supports to the one or more external horizontal protrusions thereby providing a tight seal of the flow restrictor to the inside wall of the bottle neck.

These primary and other objects of the invention will be apparent from the following description of the preferred embodiments of the invention and from the accompanying drawings.

BRIEF DESCRIPTION OF THE DRAWINGS

The following detailed description of the specific non-limiting embodiments of the present invention can be best understood when read in conjunction with the following drawings, where like structures are indicated by like reference numbers.

Referring to the drawings.

DETAILED DESCRIPTION OF THE PREFERRED EMBODIMENTS

Figure 1:
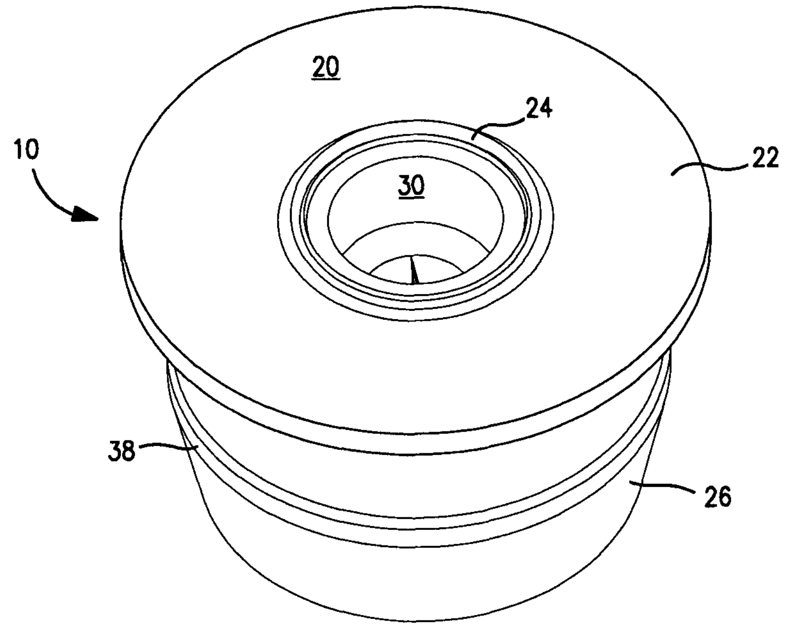
FIG. 1 is a top perspective view of the flow restrictor invention for use with a syringe for dispensing medicine.

The present invention is directed to flow restrictors for use in a medicine bottle including for dispensing medicine to infants and children. The invention provides an improved flow restrictor which prevents the accidental dispensing of the liquid medicine or the leaking of the medicine from the bottle. The invention may be used with a syringe for dispensing the medicine to an infant or child or without a syringe for dispensing the medicine to a dose cup by squeezing the bottle. As seen in the drawings and hereafter, three embodiments of the flow restrictor invention are disclosed, although it is understood that other embodiments using the invention may be made by those skilled in the art without departing from the scope of the invention.

FIGS. 1-6 show a first embodiment of the invention for use with a syringe; e.g. a 20 mm flow restrictor. FIGS. 7-11 show a second embodiment of the invention for dispensing the medicine to a dose cup by squeezing the bottle; e.g. a 24 mm flow restrictor to be used with a dose cup. FIGS. 12-16 show a third embodiment of the invention similar to the second embodiment for dispensing of the medicine to a dose cup by squeezing the bottle; e.g. a 24 mm flow restrictor to be used with a dose cup.

Figure 5:
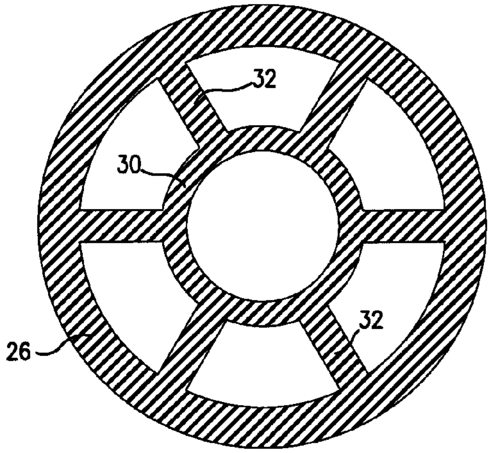
FIG. 5 is a cross-section taken along line 5-5 of FIG. 4.
Figure 6:
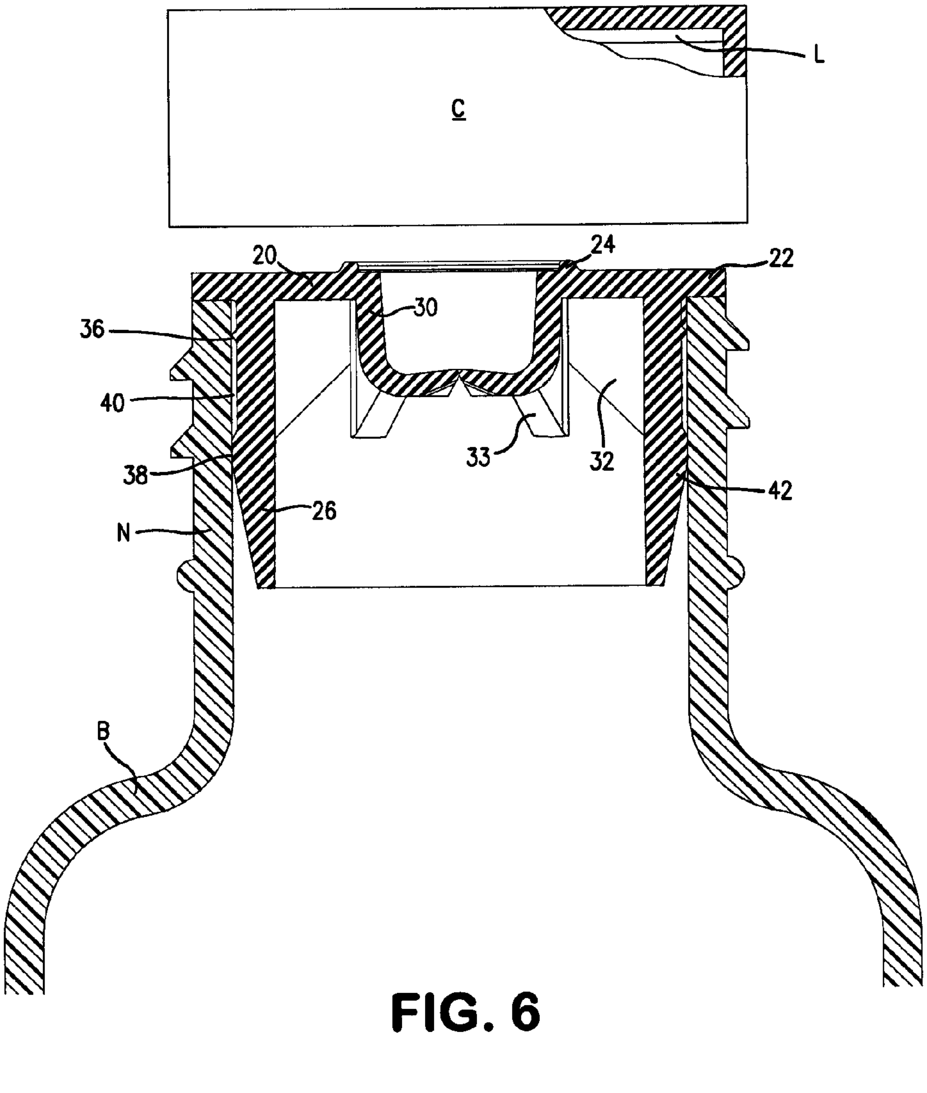
FIG. 6 is a cross-section of the flow restrictor of FIG. 1 taken along lines 6-6 of FIG. 3, a partial cross-section of a bottle and a cap in partial cross-section.
Figure 7:
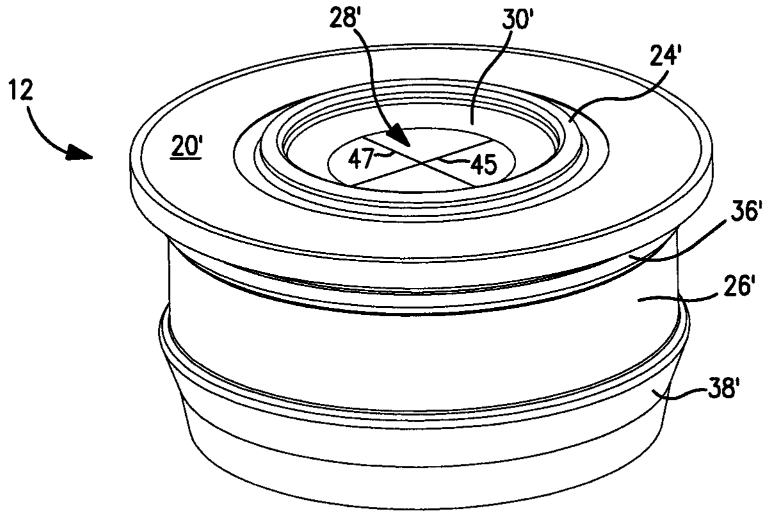
FIG. 7 is a top perspective view of a squeeze flow restrictor of the present invention for squeeze dispensing of medicine from a bottle.

Referring to FIGS. 1-6, there is disclosed a flow restrictor of the present invention for use with a syringe (not shown) for dispensing liquid medicine from a bottle. The flow restrictor 10 is inserted into the bottle B and a cap C is used to close the bottle. Referring to these figures, the flow restrictor 10 includes a cover 20 having a flange 22 adapted to seat on the opening on a bottle B as shown in FIG. 6. The cover 20 includes a raised ring 24. Ring 24 is adapted to engage the liner L of a cap C for the bottle when the cap is turned onto the bottle. The cover includes an integral downwardly extending sleeve 26 which fits into neck N of bottle B and is adapted to provide a tight seal of the flow restrictor in the bottle B, thereby precluding accidental removal of the flow restrictor from the bottle B or dislodgement of the flow restrictor from the bottle. There is a self-sealing orifice 28 for dispensing the medicine from the bottle. This orifice includes a downwardly extending annular cylinder 30 with a bottom wall 31. Vertical supports or ribs 32 extend outward from the annular cylinder 30 and engage the inside wall of the sleeve 26. The orifice 28 has a self-sealing opening 34, discussed further below, for dispensing the medicine from the bottle. The sleeve includes one or more external horizontal protrusions 36 and 38 which engage the inside wall of the neck N of the bottle B for assisting in a tight seal of the flow restrictor 10 in the bottle B.

Figure 2:
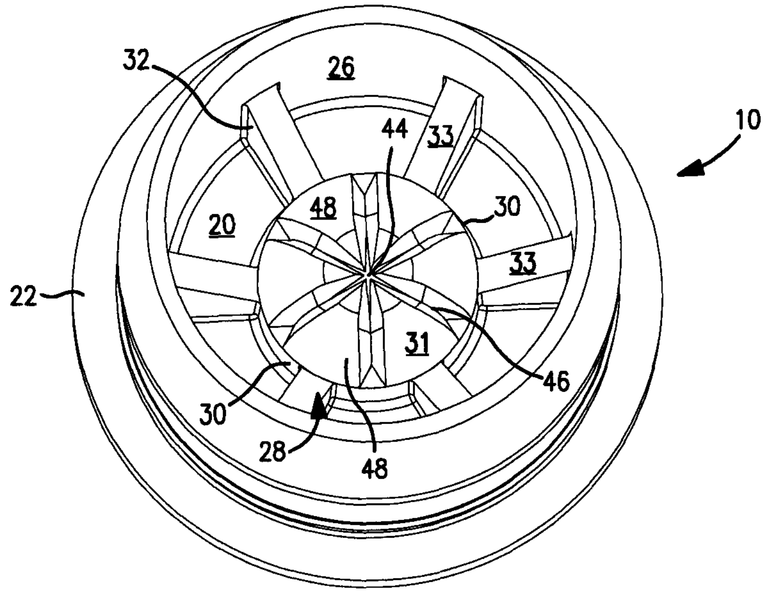
FIG. 2 is a bottom perspective view of the flow restrictor of FIG. 1.
Figure 3:
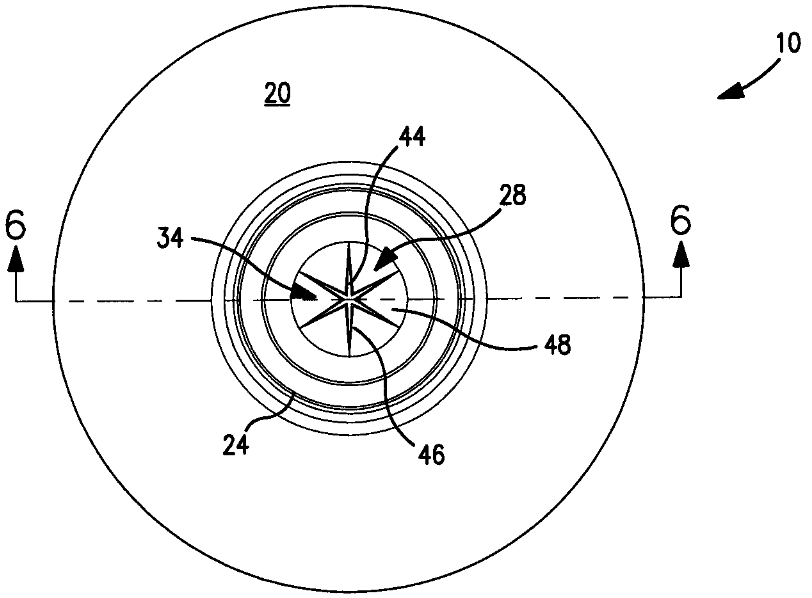
FIG. 3 is a top view of the flow restrictor of FIG. 1.
Figure 4:
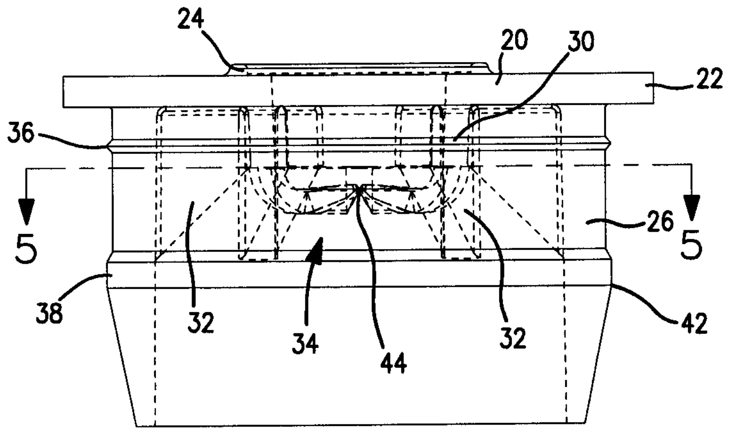
FIG. 4 is a side view of the flow restrictor of FIG. 1 showing in broken lines aspects of the present invention.

With reference to FIGS. 6 and 2, it is seen that the ring 24 is in substantially vertical alignment with the outside wall of annular cylinder 30 and where ribs 32 engage annular cylinder 30. As discussed below, the downward force of cap C on ring 24 is transferred to ribs 32. Additionally, ring 24 provides rigidity to the orifice 28 such that when a syringe is removed from the orifice, flow restrictor 10 will not be dislodged from the bottle; e.g. without the ring 24, the syringe may be removed at such an angle as to pry the flow restrictor from the bottle.

The sleeve 26 of flow restrictor 10 includes a first external horizontal protrusion 36 and a second external horizontal protrusion 38 for engaging the inside wall of neck N of bottle B as shown in FIG. 6. This provides for a slight opening 40. Additionally, the sleeve 26 extends inwardly from point 42 of the inside wall of neck N, thereby allowing for ease of insertion of the flow restrictor 10 into the bottle B.

As seen in FIGS. 2 and 5, there are preferably six ribs 32 which extend outward from the annular cylinder 30. The ribs 32 preferably extend downwardly providing a bottom wall 33 which extends from cylinder 30 to the inside wall of sleeve 26 at approximately a 45 degree angle, thereby increasing the size of the ribs to provide support. The ribs provide support to the flow restrictor and assist in a tight seal of the flow restrictor in the bottle B as discussed below. It is understood that a different number of vertical supports 32 may be used without departing from the scope of the invention.

The self-sealing orifice 28 includes a central opening 44 and six slits 46 which provide for six panels 48, thereby providing for a resilient self-sealing opening for receiving a syringe. The bottom wall 31 is thinner in dimension and the slits 46 have a groove shape, thereby providing for resiliency of the self-sealing opening. This allows for insertion of a syringe (not shown) through opening 44 to remove medicine from bottle B. The opening 44 remains closed and sealed except when a syringe is inserted and then the panels 48 move downwardly providing an enlarged opening 44 for receiving the syringe. When the syringe is removed the resilient panels 48 move back to their original position to provide a sealed opening.

When the cap C is screwed onto the bottle B, the downward force of the cap is transferred to the vertical supports 32 and to the external horizontal protrusions 36 and 38. This provides a tight seal of the flow restrictor to the inside wall of the neck of the bottle. The ring 24 prevents the liner L of cap C from deforming or otherwise interfering with orifice 28. When the cap is off of the bottle, the flow restrictor will remain secured in the bottle neck and is not subject to accidental removal or being pulled out of the bottle when the syringe is removed from the flow restrictor.

The flow restrictor is preferably made of a thermoplastic material such as polyethylene or polypropylene by known molding techniques, a preferred material being low density polyethylene.

Figure 11:
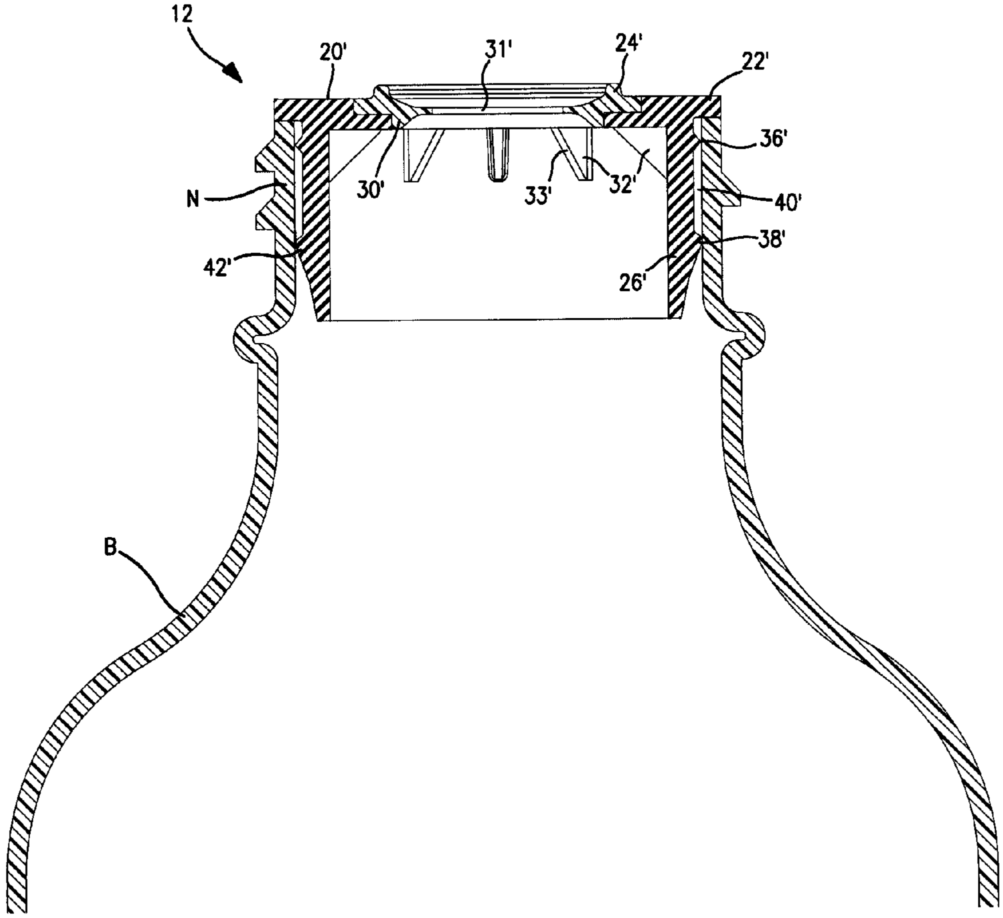
FIG. 11 is a cross-section of the flow restrictor of FIG. 8 taken along lines 11-11 of FIG. 9 and a partial cross-section of a bottle.
Figure 12:
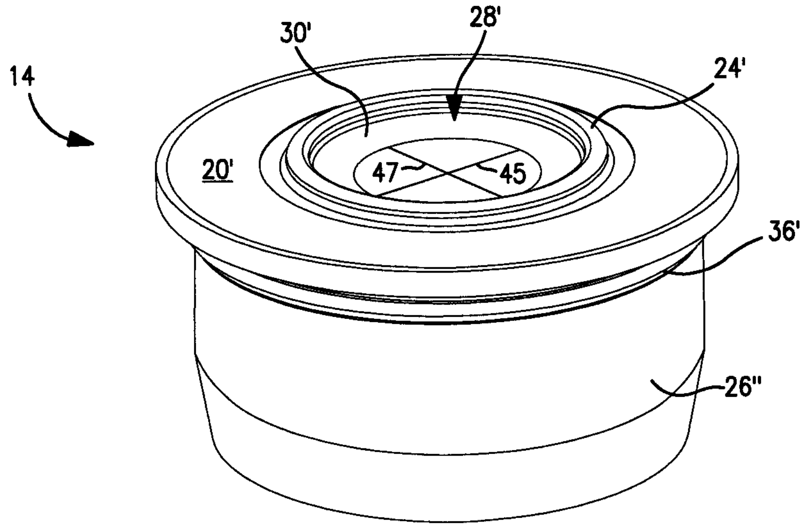
FIG. 12 is a top perspective view of an alternate embodiment of a flow restrictor of the present invention for squeeze dispensing of medicine from a bottle.
Figure 13:
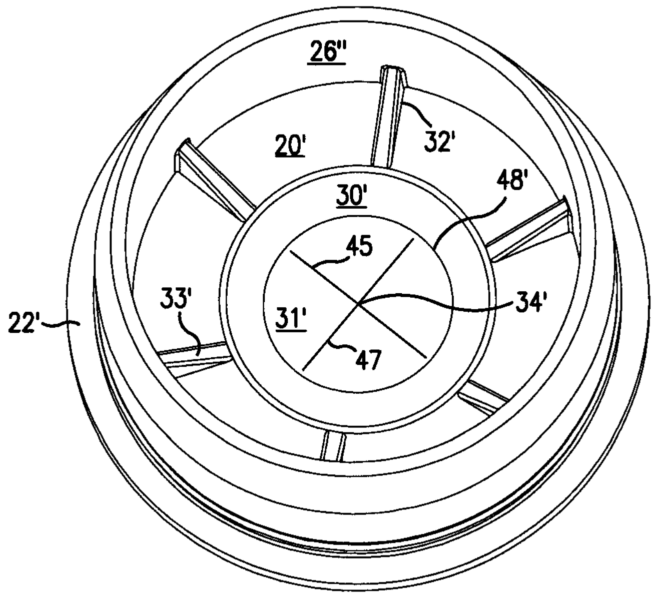
FIG. 13 is a bottom perspective view of the flow restrictor of FIG. 12.
Figure 14:
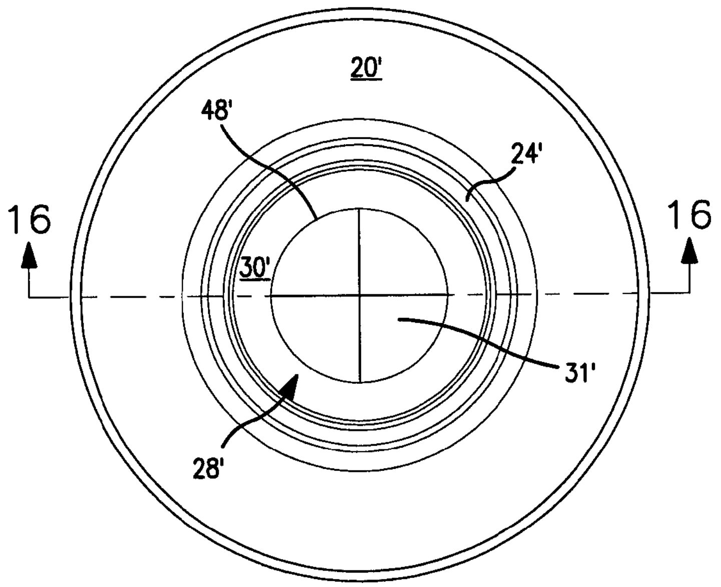
FIG. 14 is a top view of the flow restrictor of FIG. 12.
Figure 15:
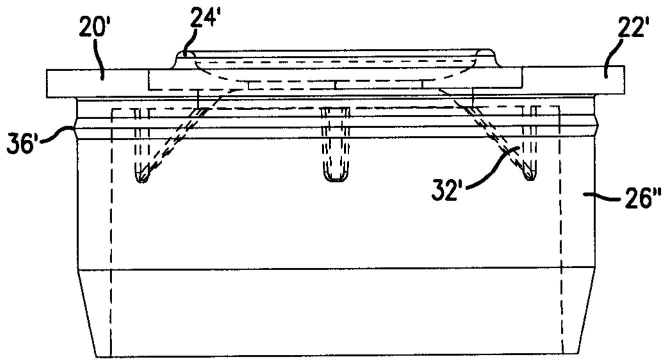
FIG. 15 is side view of the flow restrictor of FIG. 12 showing in broken lines aspects of the present invention.
Figure 16:
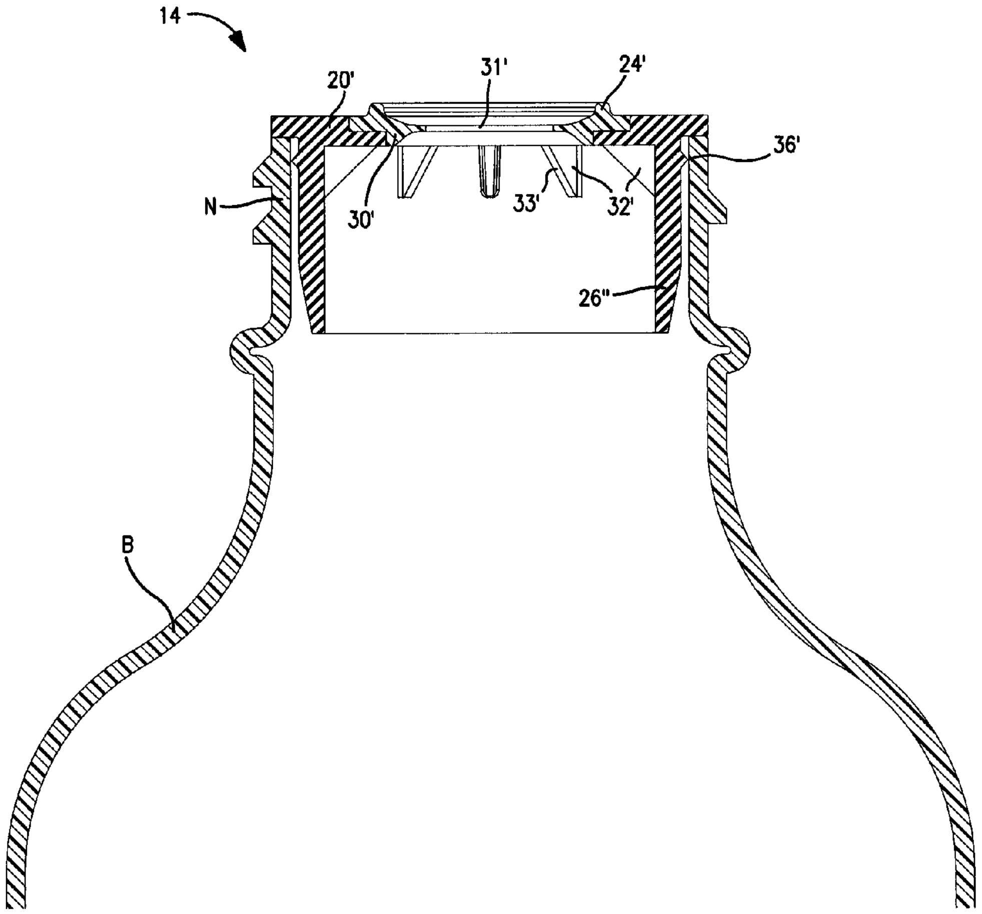
FIG. 16 is a cross-section of the flow restrictor of FIG. 12 taken along lines 16-16 of FIG. 14 and a partial cross-section of a bottle.

Referring to FIGS. 7-11 there is shown a flow restrictor 12 for squeeze dispensing of the medicine to a dose cup and using similar aspects of the invention referenced in FIGS. 1-6. The flow restrictor 12 is inserted into the bottle B and a cap (not shown, but similar to cap C of FIG. 6) is used to close the bottle. Referring to these figures, the flow restrictor 12 includes a cover 20' having a flange 22' adapted to seat on the opening on a bottle B as shown in FIG. 11. The cover 20' includes a raised ring 24'. Ring 24' is adapted to engage the liner of a cap C for the bottle when the cap is turned onto the bottle. The cover includes an integral downwardly extending sleeve 26' which fits into neck N of bottle B and is adapted to provide a tight seal of the flow restrictor in the bottle B, thereby precluding accidental removal of the flow restrictor from the bottle B or dislodgement of the flow restrictor from the bottle. There is a self-sealing orifice 28' for dispensing the medicine from the bottle. This orifice includes a downwardly extending annular cylinder 30' with a bottom wall 31'. Vertical supports or ribs 32' extend outward from the annular cylinder 30' and engage the inside wall of the sleeve 26'. The ribs 32' extend downwardly at approximately a 45 degree angle, thereby increasing the size of the ribs to provide support. The orifice 28' has a self-sealing opening 34', discussed further below, for dispensing the medicine from the bottle to a dose cup. The sleeve includes one or more external horizontal protrusions 36' and 38' which engage the inside of the neck N of the bottle B for assisting in providing a tight seal of the flow restrictor 12 in the bottle B.

Figure 8:
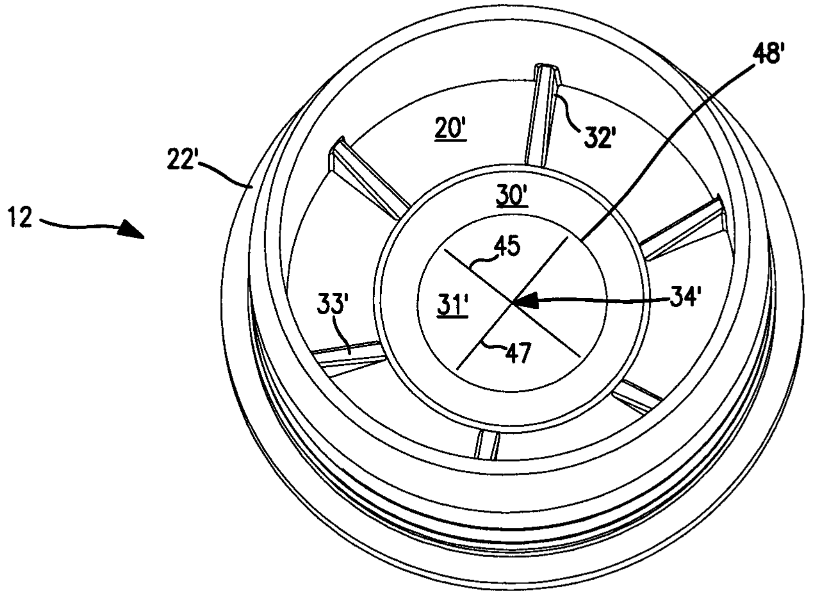
FIG. 8 is a bottom perspective view of the flow restrictor of FIG. 7.
Figure 9:
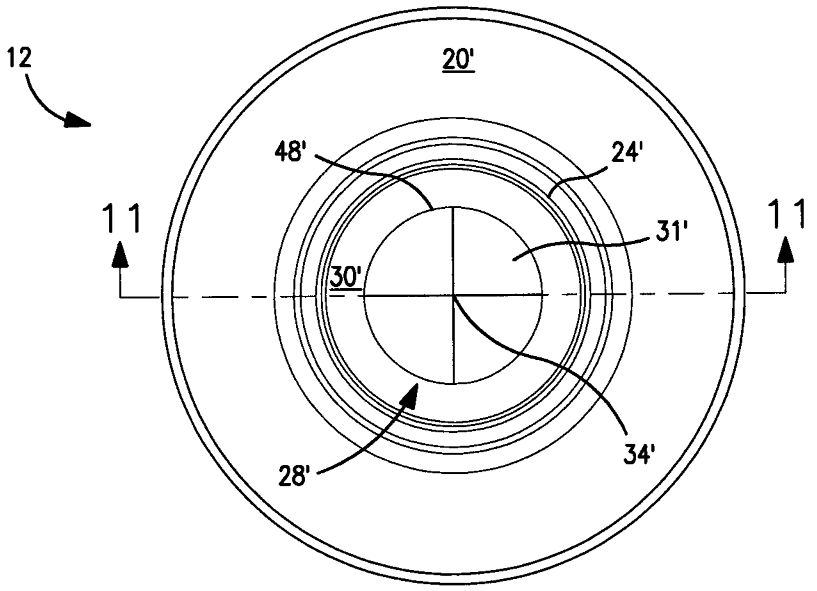
FIG. 9 is a top view of the flow restrictor of FIG. 8.
Figure 10:
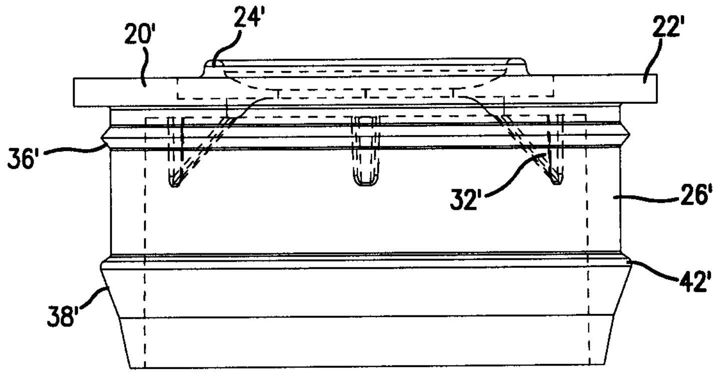
FIG. 10 is side view of the flow restrictor of FIG. 8 showing in broken lines aspects of the present invention.

With reference to FIGS. 11 and 8, it is seen that the ring 24' is in substantially vertical alignment with the outside wall of annular cylinder 30' and where ribs 32' engage annular cylinder 30'. As discussed below, the downward force of cap C on ring 24' is transferred to ribs 32'.

The sleeve 26' of flow restrictor 12 includes a first external horizontal protrusion 36' and a second external horizontal protrusion 38' for engaging the inside wall of neck N of bottle B as shown in FIG. 11. This provides for a slight opening 40'. Additionally, the sleeve 26' extends inwardly from point 42' of the inside wall of neck N, thereby allowing for ease of insertion of the flow restrictor 12 into bottle B.

As seen in the Figures, there are preferably six ribs 32' which extend outward from the annular cylinder 30'. The ribs 32' preferably extend downwardly providing a wall 33' at approximately a 45 degree angle. The ribs provide support to the flow restrictor and assist in a tight seal of the flow restrictor in the bottle B. It is understood that a different number of vertical supports 32' may be used without departing from the scope of the invention.

The self-sealing orifice 28' includes an opening 34' formed by slits 45 and 47 which provide for a resilient self-sealing opening in the surrounding circular area 48'. The bottom wall 31' is thinner in dimension, e.g. to provide resiliency to the orifice 28' for ease of opening. The opening 34' remains closed and sealed except when the bottle is squeezed and then the slits 45 and 47 move outwardly providing an enlarged opening 34' for dispensing the liquid medicine to a dosing cap. When the squeezing pressure is released, the orifice 28' closes and slits 45 and 47 move back to their original position to provide a sealed opening.

When the cap is screwed onto the bottle B, the downward force of the cap is transferred to the vertical supports 32' and to the external horizontal protrusions 36' and 38'. This provides a tight seal of the flow restrictor to the inside wall of the bottle neck. When the cap is off of the bottle, the flow restrictor will remain secure in the bottle neck and is not subject to accidental removal or being dislodged from the bottle during or after dispensing of the medicine.

The flow restrictor is preferably made of a combination thermoplastic elastomer material and a thermoplastic material and by known molding techniques. In a preferred embodiment, as seen in FIG. 11, the flow restrictor 12 is co-extruded and the cover 20' and sleeve 26' are polypropylene and the ring 24' and annular cylinder 30' are Dyna-Flex™ G2711-1000-00 thermoplastic elastomer made by PolyOne Corporation. The co-extruded flow restrictor provides a more robust support while providing a resilient opening at the self-sealing orifice 28'.

Referring now to FIGS. 12-16, there is shown a third embodiment of the flow restrictor of the present invention. This flow restrictor 14 is substantially similar to embodiment shown in FIGS. 7-11 and is also used for squeeze dispensing of medicine from a bottle to a dose cup. In this embodiment, the sleeve 26" is of a different configuration and includes only one external protrusion 36', the other aspects of this embodiment being the same as disclosed in FIGS. 7-11.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. A flow restrictor for a medicine bottle for use with a syringe and without a syringe comprising a cover having a flange adapted to seat on the opening of the bottle;

the cover having a raised ring adapted to engage the liner of a cap for the bottle when the cap is turned onto the bottle;

the cover further comprising an integral downwardly extending sleeve which fits into a neck of the bottle and adapted to provide a tight seal;

a self-sealing orifice for dispensing of the medicine comprising a downwardly extending annular cylinder having vertical supports which extend outward and engage the inside wall of the sleeve;

said orifice have a self-sealing opening for dispensing the medicine;

and said sleeve further comprising one or more external horizontal protrusions;

wherein when the cap is screwed onto the bottle, the downward force is transferred by the vertical supports to the one or more external horizontal protrusions thereby providing a tight seal of the flow restrictor to the inside wall of the bottle neck.

2. A flow restrictor according to claim 1 wherein said sleeve comprises two external horizontal protrusions.

3. A flow restrictor according to claim 1 wherein said downwardly extending annular cylinder includes six vertical supports.

4. A flow restrictor according to claim 2 wherein said downwardly extending annular cylinder includes six vertical supports.

5. A flow restrictor according to claim 4 wherein said vertical supports extend downwardly from said downwardly extending annular cylinder.

6. A flow restrictor according to claim 5 wherein said downwardly extending vertical supports are at an angle of about 45 degrees.

7. A flow restrictor according to claim 1 wherein said flow restrictor is for a medicine bottle for use with a syringe and said self-sealing orifice includes a plurality of slits adapted to form a plurality of panels providing for a self-sealing orifice adapted to open downwardly into said bottle upon the insertion of said syringe.

8. A flow restrictor according to claim 7 wherein said plurality of slits comprises six slits and said plurality of panels comprises six panels.

9. A flow restrictor according to claim 7 wherein said flow restrictor is made from a thermoplastic material selected from the group consisting of low density polyethylene, polyethylene and polypropylene.

10. A flow restrictor according to claim 1 wherein said flow restrictor is for a medicine bottle for use without a syringe for dispensing said medicine by squeezing said bottle and said self-sealing orifice comprises two intersecting slits adapted to open outwardly upon squeezing of said bottle to dispense said medicine.

11. A flow restrictor according to claim 10 wherein the flow restrictor is co-extruded and said cover and downwardly extending sleeve are polypropylene and said self-sealing orifice is a thermoplastic elastomer.

12. A flow restrictor according to claim 1 wherein said raised ring is in substantially vertical alignment with the outside wall of said downwardly extending annular cylinder and where said vertical supports engage said outside wall of said downwardly extending annular cylinder.

* * * * *